(12) United States Patent
Feng et al.

(10) Patent No.: US 11,986,024 B2
(45) Date of Patent: May 21, 2024

(54) ELECTRONIC CIGARETTE ASSEMBLY

(71) Applicant: LUXSHARE PRECISION INDUSTRY CO., LTD., Shenzhen (CN)

(72) Inventors: Yun Feng, Shenzhen (CN); Huabing Li, Shenzhen (CN); Yu Huang, Shenzhen (CN)

(73) Assignee: LUXSHARE PRECISION INDUSTRY CO., LTD., Shenzhen (CN)

( * ) Notice: Subject to any disclaimer, the term of this patent is extended or adjusted under 35 U.S.C. 154(b) by 259 days.

(21) Appl. No.: 17/571,857

(22) Filed: Jan. 10, 2022

(65) Prior Publication Data

US 2022/0322750 A1 Oct. 13, 2022

(30) Foreign Application Priority Data

Apr. 12, 2021 (CN) .......................... 202120736393.8

(51) Int. Cl.
*A24F 40/85* (2020.01)
*A24F 15/01* (2020.01)
*A24F 15/18* (2006.01)
*A24F 40/95* (2020.01)
*A61L 2/10* (2006.01)

(52) U.S. Cl.
CPC .............. *A24F 40/85* (2020.01); *A24F 15/01* (2020.01); *A24F 15/18* (2013.01); *A24F 40/95* (2020.01); *A61L 2/10* (2013.01); *A61L 2202/11* (2013.01)

(58) Field of Classification Search
CPC .......... A24F 40/85; A24F 15/01; A24F 15/18; A24F 40/95
See application file for complete search history.

(56) References Cited

U.S. PATENT DOCUMENTS

| | | | |
|---|---|---|---|
| 2013/0167854 A1* | 7/2013 | Shin | A24F 40/42 131/329 |
| 2014/0291179 A1* | 10/2014 | Xiang | B65D 25/00 206/216 |
| 2021/0120870 A1* | 4/2021 | Zhu | A24F 40/10 |

FOREIGN PATENT DOCUMENTS

CN 112089117 A 12/2020

* cited by examiner

*Primary Examiner* — Christopher M Rodd
*Assistant Examiner* — Jennifer A Kessie
(74) *Attorney, Agent, or Firm* — McNees Wallace & Nurick LLC

(57) ABSTRACT

The electronic cigarette assembly includes a cigarette case, a cigarette rod, a disinfection device, and a plurality of cartridges. The cigarette case is provided with an electronic cigarette accommodation groove and a plurality of cartridge accommodation grooves. One cartridge of the plurality of cartridges is capable of being selected to be detachably connected to the cigarette rod to form an electronic cigarette, the electronic cigarette is capable of being accommodated in the electronic cigarette accommodation groove, and remaining cartridges of the plurality of cartridges are accommodated in the plurality of cartridge accommodation grooves in one-to-one correspondence. The disinfection device is disposed in the electronic cigarette accommodation groove and configured to disinfect the one cartridge on the electronic cigarette.

11 Claims, 3 Drawing Sheets

ELECTRONIC CIGARETTE ASSEMBLY

CROSS-REFERENCE TO RELATED APPLICATION(S)

This application claims priority to Chinese Patent Application No. 202120736393.8 filed Apr. 12, 2021, the disclosure of which is incorporated herein by reference in its entirety.

TECHNICAL FIELD

The present disclosure relates to the technical field of electronic cigarettes, and in particular, to an electronic cigarette assembly.

BACKGROUND

An electronic cigarette is an electronic product that imitates cigarettes. The electronic cigarette is a kind of product that uses a battery to power and drive an atomizer, heats e-liquid in a heating tank, turns the e-liquid into steam, and then allows users to smoke.

Since the electronic cigarette can be reused for many times, a mouthpiece on a cartridge enters the mouth of a user for many times. However, the current electronic cigarette is not equipped with a special and portable disinfection device to kill germs on the mouthpiece so that the body of the user is easily to be affected due to hygiene problems.

Therefore, there is an urgent need for an electronic cigarette assembly to solve the above-mentioned technical problems.

SUMMARY

The present disclosure provides an electronic cigarette assembly which can disinfect the electronic cigarette at any time and avoid causing influence on the body of a user due to hygiene problems.

The present disclosure adopts technical solutions described below.

An electronic cigarette assembly includes a cigarette case, a cigarette rod, a plurality of cartridges, and a disinfection device.

The cigarette case is provided with an electronic cigarette accommodation groove and a plurality of cartridge accommodation grooves.

One cartridge of the plurality of cartridges is capable of being selected to be detachably connected to the cigarette rod to form an electronic cigarette, the electronic cigarette is capable of being accommodated in the electronic cigarette accommodation groove, and remaining cartridges of the plurality of cartridges are accommodated in the plurality of cartridge accommodation grooves in one-to-one correspondence.

The disinfection device is disposed in the electronic cigarette accommodation groove and configured to disinfect the cartridge on the electronic cigarette.

Figure 1:
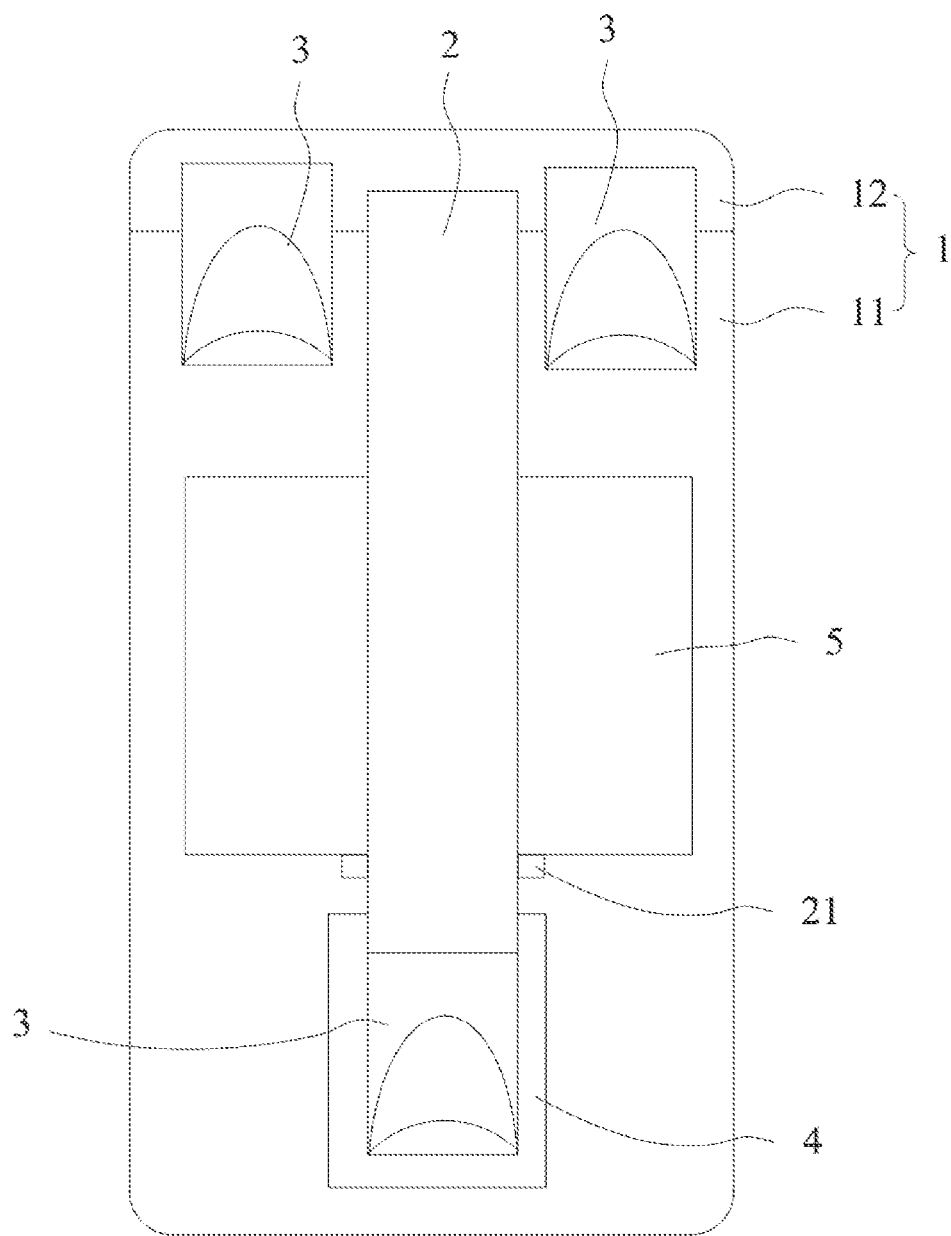
FIG. 1 is a perspective view of an electronic cigarette assembly according to an embodiment of the present disclosure.

REFERENCE LIST 1 cigarette case
2 cigarette rod
3 cartridge
4 disinfection device
5 battery assembly
11 base
12 flip cover
21 charging contact
111 electronic cigarette accommodation groove
112 cartridge accommodation groove
113 disinfection status indicator lamp
114 charging status indicator lamp
115 battery charging port

DETAILED DESCRIPTION

Embodiments of the present disclosure are described in detail below. Examples of the embodiments are illustrated in the drawings, where the same or similar reference numerals indicate the same or similar elements, or elements having the same or similar functions. The embodiments described below with reference to the drawings are exemplary, intended to explain the present disclosure.

In the description of embodiments of the present disclosure, unless otherwise expressly specified and limited, the term "connected to each other", "connected" or "mounted" is to be construed in a broad sense, for example, as connected in a mounting mode, detachably connected, mechanically connected or electrically connected, directly connected to each other or indirectly connected to each other via an intermediary, or internally connected or interactional between two components. For those of ordinary skill in the art, specific meanings of the above terms in the present disclosure can be understood according to specific conditions.

In the description of the present disclosure, unless otherwise expressly specified and limited, when a first feature is described as "on" or "below" a second feature, the first feature and the second feature may be in direct contact, or be in contact via another feature between the two features instead of being in direct contact. Moreover, when the first feature is described as "on", "above" or "over" the second feature, the first feature is right on, above or over the second feature or the first feature is obliquely on, above or over the second feature, or the first feature is simply at a higher level than the second feature. When the first feature is described as "under", "below" or "underneath" the second feature, the first feature is right under, below or underneath the second feature or the first feature is obliquely under, below or underneath the second feature, or the first feature is simply at a lower level than the second feature.

Solutions of the present disclosure are further described below through embodiments in conjunction with the drawings.

As shown in FIGS. 1 to 4, this embodiment provides an electronic cigarette assembly. The electronic cigarette assembly includes a cigarette case 1, a cigarette rod 2, a plurality of cartridges 3 and a disinfection device 4. The cigarette case 1 is provided with an electronic cigarette accommodation groove 111 and a plurality of cartridge accommodation grooves 112. One cartridge of the plurality of cartridges 3 is capable of being selected to be detachably connected to the cigarette rod 2 to form an electronic cigarette, the electronic cigarette is capable of being accommodated in the electronic cigarette accommodation groove 111, and remaining cartridges of the plurality of cartridges 3 are accommodated in the plurality of cartridge accommodation grooves 112 in one-to-one correspondence. The disinfection device 4 is disposed in the electronic cigarette accommodation groove 111 and configured to disinfect the cartridge 3 on the electronic cigarette.

The cartridge 3 includes an atomizer and a mouthpiece disposed at one end of the atomizer. Another end of the atomizer is connected to the cigarette rod 2 so that the cartridge 3 is connected to the cigarette rod 2 to form the electronic cigarette. The cigarette rod 2 is provided with a first battery for supplying power to the atomizer. In order to prevent germs from entering the mouth of a user, the cartridge 3 needs to be disinfected.

In the electronic cigarette assembly provided by this embodiment, when the electronic cigarette is not inhaled, the electronic cigarette is accommodated in the cigarette case 1 so that the electronic cigarette is convenient to carry and can be avoided from being contaminated with external dirt. At the same time, the disinfection device 4 in the electronic cigarette accommodation groove 111 can disinfect the cartridge 3 on the electronic cigarette, thereby further ensuring the cleanliness of the cartridge 3. The plurality of cartridges 3 are accommodated such that continuous use can be ensured through replacement of the cartridge 3 when the used cartridge 3 is damaged or the disinfection device 4 fails, thereby improving the user experience. Therefore, the electronic cigarette assembly provided by this embodiment can disinfect the electronic cigarette at any time and avoid causing influence on the body of the user due to hygiene problems.

Optionally, the plurality of cartridges 3 may be set to different tastes so that the user can enjoy a smoking experience of different tastes by changing the cartridge 3.

In one embodiment, the cigarette case 1 includes a base 11 and a flip cover 12, the electronic cigarette accommodation groove 111 and the plurality of cartridge accommodation grooves 112 each are disposed on a top surface of the base 11, and the flip cover 12 is configured to cover the top surface of the base 11 in an openable manner. The flip cover 12 is provided such that the electronic cigarette and the remaining cartridges 3 can be fixed, thereby, facilitating carrying.

In one embodiment, the electronic cigarette accommodation groove 111 and the plurality of cartridge accommodation grooves 112 each extend in a direction perpendicular to the top surface of the base 11, the electronic cigarette is capable of being inserted into the electronic cigarette accommodation groove 111 in the direction perpendicular to the top surface of the base 11, and the remaining cartridges 3 are capable of being inserted into the plurality of cartridge accommodation grooves 112 in the direction perpendicular to the top surface of the base 11. This configuration can improve the stability of placing the electronic cigarette and the cartridges 3 and avoids the occurrence of the electronic cigarette and the cartridges 3 falling due to the small angle inclination of the base 11.

In order to further improve the stability of placement, a length of the electronic cigarette accommodation groove 111 is greater than half of a length of the electronic cigarette and less than the length of the electronic cigarette. The length of the electronic cigarette accommodation groove 111 is greater than half of the length of the electronic cigarette so that a center of gravity of the electronic cigarette is located in the electronic cigarette accommodation groove 111, thereby ensuring the stability of placement. The length of the electronic cigarette accommodation groove 111 is less than the length of the electronic cigarette so that one end of the electronic cigarette is located outside the electronic cigarette accommodation groove 111, and thus an exposed end of the electronic cigarette is pinched for conveniently extracting the electronic cigarette. Therefore, this arrangement facilitates taking and placing and improves the stability of placement. Similarly, a length of each cartridge accommodation groove 112 is greater than half of a length of each the cartridge 3 and less than the length of each cartridge 3.

In this embodiment, the flip cover 12 is provided with bypass grooves respectively corresponding to the electronic cigarette accommodation groove 111 and the plurality of cartridge accommodation grooves 112 so that a part of the electronic cigarette in the electronic cigarette accommodation groove 111 and a part of each cartridge 3 in each cartridge accommodation groove 112 extend into the corresponding bypass grooves when the flip cover 12 is fastened to the base 11.

In one embodiment, the disinfection device 4 is disposed at a bottom of the electronic cigarette accommodation groove 111, and one end of the electronic cigarette provided with the cartridge 3 faces a groove bottom of the electronic cigarette accommodation groove 111. The cartridge 3 is inserted into the bottom of the electronic cigarette accommodation groove 111 and placed in a disinfection range of the disinfection device 4 such that the cartridge 3 is disinfected. In this embodiment, the disinfection device 4 includes an extreme ultraviolet light emitter. The extreme ultraviolet light emitted by the extreme ultraviolet light emitter irradiates the cartridge 3 so that germs on the cartridge 3 are killed. Apparently, the disinfection device 4 may also be other types of sterilizable light emitters or a disinfection device spraying a disinfection spray.

Figure 2:
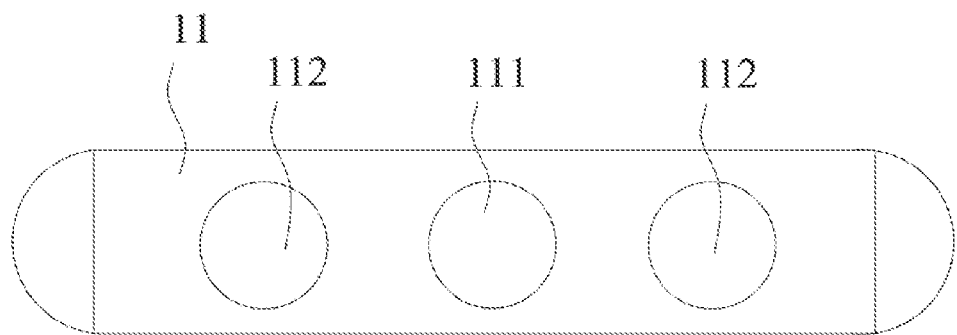
FIG. 2 is a top view of a base according to an embodiment of the present disclosure.
Figure 3:
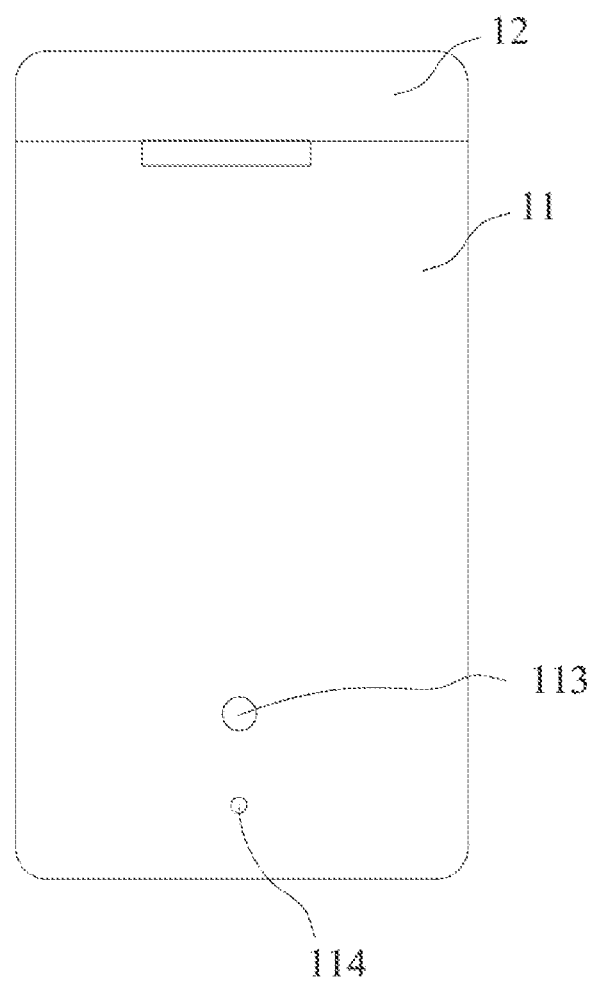
FIG. 3 is a front view of an electronic cigarette assembly according to an embodiment of the present disclosure.

In one embodiment, a number of the plurality of cartridge accommodation grooves 112 is an even number, the plurality of cartridge accommodation grooves 112 are evenly divided into two groups, and the two groups of cartridge accommodation grooves 112 are respectively disposed on two sides of the electronic cigarette accommodation groove 111. In this embodiment, as shown in FIG. 2, the electronic cigarette accommodation groove 111 is disposed in a middle position of the top surface of the base 11, two cartridge accommodation grooves 112 are provided, and the two cartridge accommodation grooves 112 are symmetrically disposed with respect to the electronic cigarette accommodation groove 111 such that the cigarette case 1 has a symmetrical structure and is more convenient to use.

The base 11 is provided with a battery assembly 5, and the battery assembly 5 is disposed between the cartridge accommodation grooves 112 and the disinfection device 4 so that the overall structure is compact and an occupied space is small. The battery assembly 5 includes a second battery and a control circuit module electrically connected to the second battery. The second battery is configured to supply power to the disinfection device 4 and charge a first batter in the cigarette rod 2. The control circuit module is configured to control the charge and discharge of the second battery, and the control of the battery by the control circuit module is a conventional arrangement in the art and is repeated herein.

In one embodiment, an inner wall of the electronic cigarette accommodation groove 111 is provided with an electronic cigarette charging port, the cigarette rod 2 is provided with a charging contact 21, the charging contact 21 is electrically connected to the first battery in the cigarette rod 2, and when the electronic cigarette is accommodated in the electronic cigarette accommodation groove 111, the charging contact 21 is inserted into the electronic cigarette charging port, thereby achieving the charging of the electronic cigarette.

In one embodiment, the cigarette case 1 is provided with a disinfection status indicator lamp 113. The disinfection status indicator lamp 113 turns on when the disinfection device 4 is in a disinfection state and turns off when the disinfection device 4 is in a non-disinfection state.

In this embodiment, when the electronic cigarette is inserted into the electronic cigarette accommodation groove 111, the disinfection device 4 starts to emit light for disinfection, and the disinfection device 4 automatically extinguishes after the disinfection is carried out for a preset period of time, thereby ensuring the elimination of germs and saving energy.

In one embodiment, the cigarette case 1 is provided with a charging status indicator lamp 114. The charging status indicator lamp 114 turns on when the electronic cigarette is in a charging state, and turns off when the electronic cigarette is not charged. When the electronic cigarette is inserted into the electronic cigarette accommodation groove 111, the electronic cigarette is charged, and the charging status indicator lamp 114 turns on; and after the electric quantity is full, the charging is stopped and the charging status indicator lamp 114 turns off. In this manner, whether the electric quantity of the electronic cigarette is full can be determined by observing the charging status indicator lamp 114.

Figure 4:
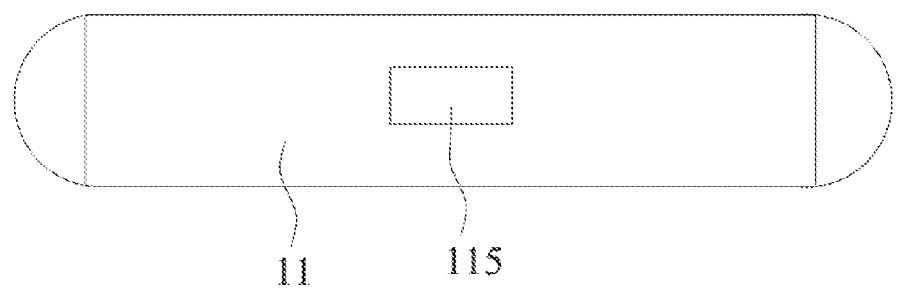
FIG. 4 is an upward view of a base according to an embodiment of the present disclosure.

As shown in FIG. 4, a bottom surface of the base 11 is provided with a battery charging port 115, the battery charging port 115 is electrically connected to the second battery of the battery assembly 5, and the electric connection between the battery charging port 115 and an external power source can be implemented by an adapted charger so that the charging of the second battery is implemented.

In one embodiment, one end of the flip cover 12 is a rotating connection end, another end is a fastening end, the rotating connection end is rotatably connected to the base 11, and the fastening end is capable of rotating about the rotating connection end to the base 11 and being fastened to the base 11. The opening and closing is achieved by flipping the flip cover 12 so that the operation is simple and quick.

In one embodiment, the rotating connection end is rotatably connected to the base 11 through a rotating shaft, and a torsion spring is sleeved on the rotating shaft. The fastening end is provided with a slot, the base 11 is provided with a buckle, and the buckle is engaged with the slot when the fastening end is rotated to and fastened to the base 11. The buckle is pressed to deviate toward a direction facing away from the slot so that the buckle is separated from the slot, and the flip cover 12 is automatically opened under the action of the torsion spring, so that the operation is more convenient.

The present disclosure provides the electronic cigarette assembly, and when the electronic cigarette is not inhaled, the electronic cigarette is accommodated in the cigarette case so that the electronic cigarette is convenient to carry and can be avoided from being contaminated with external dirt. At the same time, the disinfection device in the electronic cigarette accommodation groove can disinfect the cartridge on the electronic cigarette, thereby further ensuring the cleanliness of the cartridge. The plurality of cartridges are accommodated such that continuous use can be ensured through replacement of the cartridge when the used cartridge is damaged or the disinfection device fails, thereby improving the user experience. Therefore, the electronic cigarette assembly provided by the present disclosure can disinfect the electronic cigarette at any time and avoid causing influence on the body of the user due to hygiene problems.

What is claimed is:

1. An electronic cigarette assembly, comprising:
   a cigarette case provided with an electronic cigarette accommodation groove and a plurality of cartridge accommodation grooves;
   a cigarette rod;
   a plurality of cartridges, wherein one cartridge of the plurality of cartridges is capable of being selected to be detachably connected to the cigarette rod to form an electronic cigarette, the electronic cigarette is capable of being accommodated in the electronic cigarette accommodation groove, and remaining cartridges of the plurality of cartridges are accommodated in the plurality of cartridge accommodation grooves in one-to-one correspondence; and
   a disinfection device, wherein the disinfection device is disposed in the electronic cigarette accommodation groove and configured to disinfect the one cartridge of the plurality of cartridges on the electronic cigarette,
   wherein the cigarette case comprises a base and a flip cover, wherein the electronic cigarette accommodation groove and the plurality of cartridge accommodation grooves each are disposed on a top surface of the base, and the flip cover is configured to cover the top surface of the base in an openable manner;
   wherein the electronic cigarette accommodation groove and the plurality of cartridge accommodation grooves each extend in a direction perpendicular to the top surface of the base, the electronic cigarette is capable of being inserted into the electronic cigarette accommodation groove in the direction perpendicular to the top surface of the base, and the remaining cartridges are capable of being inserted into the plurality of cartridge accommodation grooves in the direction perpendicular to the top surface of the base; and
   wherein a length of the electronic cigarette accommodation groove is greater than half of a length of the electronic cigarette and less than the length of the electronic cigarette; and a length of each of the plurality of cartridge accommodation grooves is greater than half of a length of each of the plurality of the cartridges and less than the length of each of the plurality of the cartridges.

2. The electronic cigarette assembly of claim 1, wherein the disinfection device is disposed at a bottom of the electronic cigarette accommodation groove, and one end of the electronic cigarette provided with the cartridge is configured to face a groove bottom of the electronic cigarette accommodation groove.

3. The electronic cigarette assembly of claim 1, wherein one end of the flip cover is a rotating connection end, another end of the flip cover is a fastening end, the rotating connection end is rotatably connected to the base, and the fastening end is capable of rotating about the rotating connection end to the base and being fastened to the base.

4. The electronic cigarette assembly of claim 1, wherein a number of the plurality of cartridge accommodation grooves is an even number, the plurality of cartridge accommodation grooves are evenly divided into two groups of cartridge accommodation grooves, and the two groups of cartridge accommodation grooves are respectively disposed on two sides of the electronic cigarette accommodation groove.

5. The electronic cigarette assembly of claim 4, wherein the disinfection device is disposed at a bottom of the electronic cigarette accommodation groove, and one end of the electronic cigarette provided with the cartridge is configured to face a groove bottom of the electronic cigarette accommodation groove.

6. The electronic cigarette assembly of claim 4, wherein one end of the flip cover is a rotating connection end, another end of the flip cover is a fastening end, the rotating connection end is rotatably connected to the base, and the fastening end is capable of rotating about the rotating connection end to the base and being fastened to the base.

7. The electronic cigarette assembly of claim 1, wherein an inner wall of the electronic cigarette accommodation groove is provided with an electronic cigarette charging port, the cigarette rod is provided with a charging contact, and when the electronic cigarette is accommodated in the electronic cigarette accommodation groove, the charging contact is inserted into the electronic cigarette charging port.

8. The electronic cigarette assembly of claim 7, wherein the disinfection device is disposed at a bottom of the electronic cigarette accommodation groove, and one end of the electronic cigarette provided with the cartridge is configured to face a groove bottom of the electronic cigarette accommodation groove.

9. The electronic cigarette assembly of claim 7, wherein one end of the flip cover is a rotating connection end, another end of the flip cover is a fastening end, the rotating connection end is rotatably connected to the base, and the fastening end is capable of rotating about the rotating connection end to the base and being fastened to the base.

10. The electronic cigarette assembly of claim 1, wherein the cigarette case is provided with a disinfection status indicator lamp.

11. The electronic cigarette assembly of claim 1, wherein the cigarette case is provided with a charging status indicator lamp.

* * * * *